United States Patent
Ueno et al.

(10) Patent No.: US 7,417,067 B2
(45) Date of Patent: *Aug. 26, 2008

(54) COMPOSITION AND METHOD FOR STABILIZING THE SAME

(75) Inventors: Ryuji Ueno, Montgomery, MD (US); Tsuyoshi Habe, Sasayami (JP)

(73) Assignee: Sucampo AG, Zurich (CH)

( * ) Notice: Subject to any disclaimer, the term of this patent is extended or adjusted under 35 U.S.C. 154(b) by 229 days.

This patent is subject to a terminal disclaimer.

(21) Appl. No.: 10/383,581

(22) Filed: Mar. 10, 2003

(65) Prior Publication Data

US 2004/0235885 A1   Nov. 25, 2004

Related U.S. Application Data

(62) Division of application No. 09/688,351, filed on Oct. 16, 2000, now Pat. No. 6,583,174.

(60) Provisional application No. 60/159,549, filed on Oct. 15, 1999.

(51) Int. Cl.
*A61K 31/352* (2006.01)
*C07D 311/94* (2006.01)

(52) U.S. Cl. ..................... 514/456; 549/396

(58) Field of Classification Search .............. 549/396; 514/456

See application file for complete search history.

(56) References Cited

U.S. PATENT DOCUMENTS

| 4,247,702 A | 1/1981 | Felsch et al. |
| 4,248,867 A | 2/1981 | Ikushima |
| 5,164,415 A | 11/1992 | Ueno |
| 5,166,174 A | 11/1992 | Ueno et al. |
| 5,225,439 A | 7/1993 | Ueno et al. |
| 5,254,588 A * | 10/1993 | Ueno et al. ............... 514/573 |
| 5,284,858 A | 2/1994 | Ueno et al. |
| 5,317,032 A | 5/1994 | Ueno et al. |
| 5,380,709 A | 1/1995 | Ueno et al. |
| 5,411,952 A | 5/1995 | Kaswan |
| 5,428,062 A | 6/1995 | Ueno et al. |
| 5,474,979 A | 12/1995 | Ding et al. |
| 5,739,161 A * | 4/1998 | Ueno ............................ 514/530 |
| 5,886,034 A | 3/1999 | Ueno et al. |
| 5,981,607 A | 11/1999 | Ding et al. |
| 6,414,016 B1 | 7/2002 | Ueno |

FOREIGN PATENT DOCUMENTS

| EP | 0 284 108 A1 | 9/1988 |
| EP | 0 347 243 A1 | 12/1989 |
| EP | 0347243 | 12/1989 |
| EP | 0 353 917 A1 | 2/1990 |
| EP | 0353917 A1 | 2/1990 |
| EP | 0 467 564 A2 | 1/1992 |
| EP | 0 532 218 A1 | 3/1993 |
| EP | 0532218 B1 | 3/1993 |
| EP | 0 690 049 A2 | 1/1996 |
| HU | P8903128 A | 11/1990 |
| JP | 53-50141 | 5/1978 |
| JP | 53-75320 | 7/1978 |
| JP | 55-136219 | 10/1980 |
| JP | 59-137413 | 8/1984 |
| JP | 2-32055 A | 2/1990 |
| JP | 2-204417 | 8/1990 |
| JP | 4-46122 | 2/1992 |
| JP | 4-210631 | 7/1992 |

OTHER PUBLICATIONS

Paten Office of People's Republic of China Office Action.
Koichi Takahashi, Takashi Suzuki, Hitomi Sakano, and Nobuyasu Mizuno, Effect of Vehicles on Diclofenac Permeation across Excised Rat Skin, Biol. Pharm. Bull., vol. 18, No. 4, pp. 571-575 (1995).

* cited by examiner

*Primary Examiner*—Bernard Dentz
(74) *Attorney, Agent, or Firm*—Sughrue Mion, PLLC

(57) ABSTRACT

Disclosed is a novel composition comprising a novel bi-cyclic compound, which is expected to be pharmaceutically active, and a glyceride. The stability of the bi-cyclic compound can be improved significantly by dissolving the same in a glyceride.

34 Claims, No Drawings

COMPOSITION AND METHOD FOR STABILIZING THE SAME

This is a divisional of application Ser. No. 09/688,351 filed Oct. 16, 2000 now U.S. Pat. No. 6,583,174, which claims benefit of Provisional Application No. 60/159,549 filed Oct. 15, 1999; the above noted prior applications are all hereby incorporated by reference.

FIELD OF THE INVENTION

The present invention relates to a novel composition comprising a novel bi-cyclic compound and a glyceride, and a method for stabilizing the bi-cyclic compound comprising the step admixing the same with a glyceride.

BACKGROUND ART

A glyceride has been applied widely in the medical field and is useful as an immediate alimentation or an enteroprotecting agent (JP-A-4-210631). In addition, it is also useful as a solvent for various pharmaceutically active compounds such as active vitamin Ds, diazepam, thiazole derivatives, prostaglandins or flavonoids, as a diluent for a capsule preparation, as a vehicle of eye drop, and as a stabilizing agent (JP-A-53-50141, JP-A-53-75320, U.S. Pat. No. 4,248,867, JP-A-55-136219, U.S. Pat. No. 4,247,702, JP-A-59-137413, JP-A-02-204417, JP-A-04-46122, U.S. Pat. No. 5,411,952, U.S. Pat. No. 5,474,979 and U.S. Pat. No. 5,981,607).

However, the prior arts are silent on the effect of glycerides on the novel pharmaceutically active bi-cyclic compounds.

SUMMARY OF THE INVENTION

The object of the present invention is to provide a novel composition comprising a certain bi-cyclic compound having a pharmacological activity and a glyceride, and a method for stabilizing the bi-cyclic compound by admixing the same with a glyceride.

Another object of the present invention is to provide a novel compound having a pharmacological activity.

This inventor studied to improve the stability of a novel bi-cyclic compound and found that a composition comprising the bi-cyclic compound and a glyceride can attain the above object.

Accordingly, the present invention provides a novel composition comprising a bi-cyclic compound represented by the formula (I):

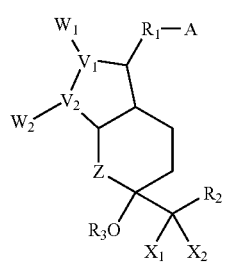

wherein, A is —CH$_2$OH, —COCH$_2$OH, —COOH or a functional derivative thereof;

X$_1$ and X$_2$ are hydrogen atom, lower alkyl or halogen atom;
V$_1$ and V$_2$ are carbon or oxygen atoms;
W$_1$ and W$_2$ are

wherein R$_4$ and R$_5$ are hydrogen atom, hydroxy, halogen atom, lower alkyl, lower alkoxy or hydroxy(lower)alkyl with the proviso that R$_4$ and R$_5$ are not hydroxy or lower alkoxy at the same time;

Z is a carbon, oxygen, sulfur or nitrogen atom;

R$_1$ is a saturated or unsaturated bivalent lower-medium aliphatic hydrocarbon residue which is unsubstituted or substituted with halogen, an alkyl group, hydroxy, oxo, aryl or heterocyclic group;

R$_2$ is a saturated or unsaturated, lower or medium aliphatic hydrocarbon residue which is unsubstituted or substituted with halogen atom, oxo, hydroxy, lower alkyl, lower alkoxy, lower alkanoyloxy, lower cycloalkyl, lower cycloalkyloxy, aryl, aryloxy, heterocyclic group or heterocyclic-oxy group; lower cycloalkyl; lower cycloalkyloxy; aryl, aryloxy, heterocyclic group or heterocyclic-oxy group;

R$_3$ is a hydrogen atom, a lower alkyl, lower cycloalkyl, aryl or heterocyclic group; and a glyceride, and a method for stabilizing the above-specified bi-cyclic compound by means of dissolving said compound in a glyceride.

The present invention also provides a novel bi-cyclic compound represented by the above formula (I).

In the above formula (I), the term "unsaturated" in the definitions for R$_1$ and R$_2$ is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 2 to 8 carbon atoms for R$_1$ and 1 to 10, especially 1 to 8 carbon atoms for R$_2$.

The term "halogen atom" covers fluorine, chlorine, bromine and iodine. Particularly preferable is a fluorine atom.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "lower cycloalkyl" refers to a cyclic group formed by cyclization of a lower alkyl group as defined above but contains three or more carbon atoms, and includes, for example, cyclopropyl, cyclobutyl, cyclopentyl and cyclohexyl.

The term "lower cycloalkyloxy" refers to the group of lower-cycloalkyl-O—, wherein lower cycloalkyl is as defined above.

The term "aryl" may include unsubstituted or substituted aromatic hydrocarbon rings (preferably monocyclic groups), for example, phenyl, naphthyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfer atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolonyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lautyl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy(lower) alkyl esters such as methoxymethyl ester and 1-methoxyethyl ester; and optionally substituted aryl esters such as, for example, phenyl ester, tosyl ester, t-butylphenyl ester, salicyl ester, 3,4-di-methoxyphenyl ester and benzamidophenyl ester; and aryl(lower)alkyl ester such as benzyl ester, trityl ester and benzhydryl ester. Examples of the amides are mono- or di-lower alkyl amides such as methylamide, ethylamide and dimethylamide; arylamides such as anilide and toluidide; and alkyl- or aryl-sulfonylamides such as methylsulfonylamide, ethylsulfonyl-amide and tolylsulfonylamide.

Preferred A is —COOH, —CH$_2$OH, or its pharmaceutically acceptable salt, ester, ether or amide.

Preferred combination of X$_1$ and X$_2$ is that at least one of X$_1$ and X$_2$ is halogen atom, and more preferably, both of them are halogen, especially fluorine atoms.

Preferred W$_1$ is =O, or where one of R$_4$ and R$_5$ is hydrogen, another is hydroxy, Preferred W$_2$ is where R$_4$ and R$_5$ are both hydrogen atoms, Preferred Z is an oxygen atom.

Preferred R$_1$ is an unsubstituted saturated or unsaturated bivalent lower-medium aliphatic hydrocarbon residue. It may preferably have 1-10 carbon atoms, more preferably, 2-8 carbon atoms.

Examples of R$_1$ include, for example, the following groups:

—CH$_2$—CH$_2$—,
—CH$_2$—CH$_2$—CH$_2$—CH$_2$—,
—CH$_2$—CH=CH—CH$_2$—,
—CH$_2$—CH$_2$—CH$_2$—CH$_2$—CH$_2$—CH$_2$—,
—CH$_2$—CH=CH—CH$_2$—CH$_2$—CH$_2$—,
—CH$_2$—CH$_2$—CH$_2$—CH$_2$—CH=CH—,
—CH$_2$—C≡C—CH$_2$—CH$_2$—CH$_2$—,
—CH$_2$—CH$_2$—CH$_2$—CH$_2$—CH(CH$_3$)—CH$_2$,
—CH$_2$—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—CH$_2$—,
—CH$_2$—CH$_2$—CH$_2$—CH$_2$—CH$_2$—CH$_2$—CH=CH—,
—CH$_2$—C≡C—CH$_2$—CH$_2$—CH$_2$—CH$_2$—CH$_2$—,
—CH$_2$—CH$_2$—CH$_2$—CH$_2$—CH$_2$—CH$_2$—CH$_2$(CH$_3$)—CH$_2$—

Preferred R$_2$ is a saturated or unsaturated bivalent lower-medium aliphatic hydrocarbon residue. It may preferably have 1-10 carbon atoms, more preferably, 1-8 carbon atoms.

Preferred R$_3$ is a hydrogen atom.

The bi-cyclic compounds according to the present invention encompass not only the compounds represented by the above formula (I) but also optic isomers, steric isomers, and tautomeric isomers thereof.

It has been known that a bi-cyclic compound having the formula as shown below (Tautomer II) may be in equilibrium with its tautomeric isomer, 13,14-dihydro-15-keto-prostaglandin compound (tautomer I) (U.S. Pat. No. 5,166,174, U.S. Pat. No. 5,225,439, U.S. Pat. No. 5,284,858, U.S. Pat. No. 5,380,709, U.S. Pat. No. 5,428,062 and U.S. Pat. No. 5,886,034, these cited references are herein incorporated by reference.)

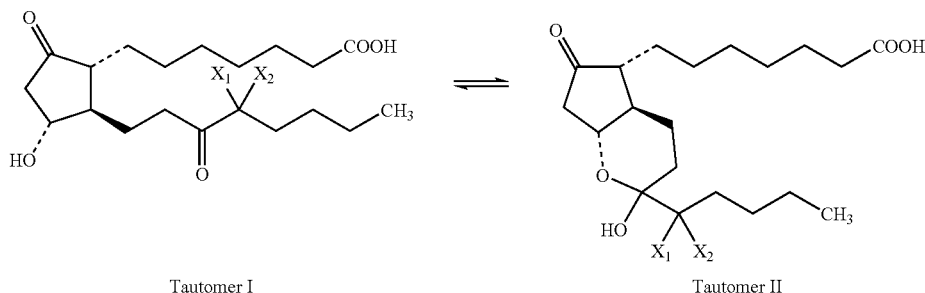

Tautomer I    Tautomer II

However, it has been discovered that in the absence of water, the tautomeric compound as above exist predominantly in the form of the bi-cyclic compound. In aqueous media, it is believed that hydrogen bonding occurs between the water molecule and, for example, the keto group at the hydrocarbon chain, thereby hindering bi-cyclic ring formation. In addition, it is believed that the halogen atom(s) at $X_1$ and/or $X_2$ promote bi-cyclic ring formation, such as the compound 1 or 2 below. The bi-cyclic/mono-cyclic structures, for example, may be present in a ratio of 6:1 in $D_2O$; 10:1 in $CD_3OD$-$D_2O$ and 96:4 in $CDCl_3$. Accordingly, a preferable embodiment of the present invention is the composition in which the bi-cyclic form is present in ratio of bi-cyclic/mono-cyclic of at least 50:50, preferably 90:10, or even greater to substantially all bi-cyclic compound; 100% bi-cyclic compound is within this invention.

Preferred embodiment of the compound of the present invention include the Compounds 1 and 2 shown below:

Compound 1:

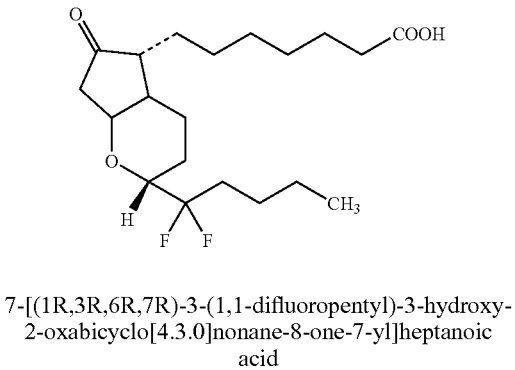

7-[(1R,3R,6R,7R)-3-(1,1-difluoropentyl)-3-hydroxy-2-oxabicyclo[4.3.0]nonane-8-one-7-yl]heptanoic acid Compound 2:

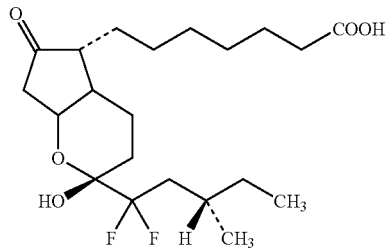

7-[(1R,6R,7R)-3-[(3S)-1,1-difluoro-3-methylpentyl]-3-hydroxy-2-oxabicyclo[4.3.0]nonane-8-one-7-yl] heptanoic acid The compounds of the present invention possess some pharmacological activities such as bronchodialator.

The above described bi-cyclic compound may prepared according to the general process set forth below: Preparation of Isopropyl 7-[(1S,3S,6S,7R)-3-heptyl-3-hydroxy-bi-cyclo[4.3.0]nonane-8-one-7-yl]hept-5-enoate and Isopropyl 7-[1S,3R,6S,7R]-3-heptyl-3-hydroxy-bicyclo[4.3.0]nonane-8-one-7-yl]hept-5-enoate 1. Preparation of Isopropyl (Z)-7-[1R,2R,3R,5S]-2-(3,3-ethylenedioxydecyl)-5-hydroxy-3-(p-toluensulfonyl)cyclopentyl]hept-5-enoate (2)

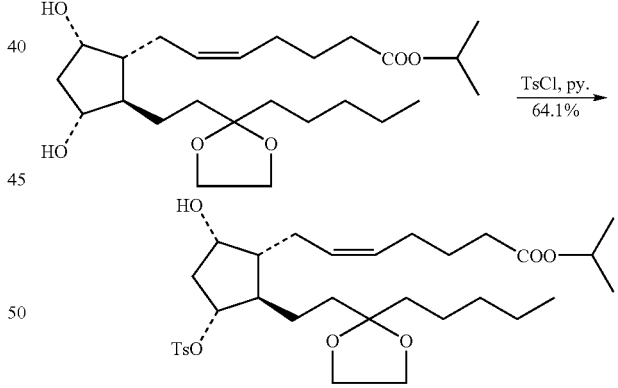

To a mixture of pyridine (0.77 g) and isopropyl (Z)-7-[(1R,2R,3R,5S)-3,5-dihydroxy-2-(3,3-ethylenedioxydecyl)cyclopentyl]hept-5-enoate (1) (4.05 g) in dichloromethane, a solution of tosyl chloride (1.86 g) in dichloromethane was added at 0° C., and stirred for 2 days at the temperature. During the reaction, each tosyl chloride (5.58 g) and pyridine (2.31 g) was added in three portions. After the usual work-up, the crude product was chromatographed on silica gel to give isopropyl (Z)-7-[(1R,2R,3R,5S)-2-(3,3-ethylenedioxydecyl)-5-hydroxy-3-(p-toluenesulfoxy)cyclopentyl]hept-5-enoate (2). Yield 3.45 g, 64.1%.

2. Preparation of Isopropyl (Z)-7-[(1R,2S)-2-(3,3-ethylenedioxydecyl)-5-oxocyclopent-3-enyl]hept-5-enoate (3)

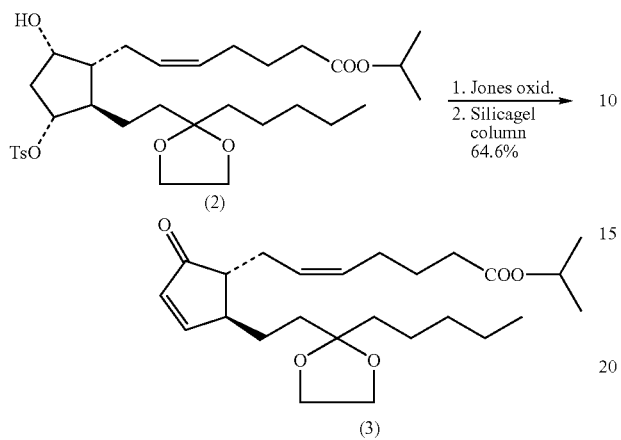

Isopropyl (Z)-[1R,2R,3R,5S]-2-(3,3-ethylenedioxy-decyl)-5-hydroxy-3-(p-toluenesulfoxy)cyclopentyl]hept-5-enoate (2) (1.72 g) was oxidized in acetone at −40° C. to −20° C. with Jones reagent for 4 hours. After the usual work-up, the crude product was passed through silica gel pad with n-hexane/ethyl acetate (3.5/1). The product was further chromatographed on silica gel (n-hexane/ethyl acetate=4/1). Isopropyl (Z)-7-[(1R,2S)-2-(3,3-ethylenedioxydecyl)-5-oxo-cyclopent-3-enyl]hept-5-enoate (3) was obtained. Yield 0.81 g, 64.6%.

3. Preparation of Isopropyl-7-[(1R,2S,3R)-2-(3,3-ethylenedioxydecyl)-3-hydroxymethyl-5-oxocyclopentyl]hept-5-enoate (4)

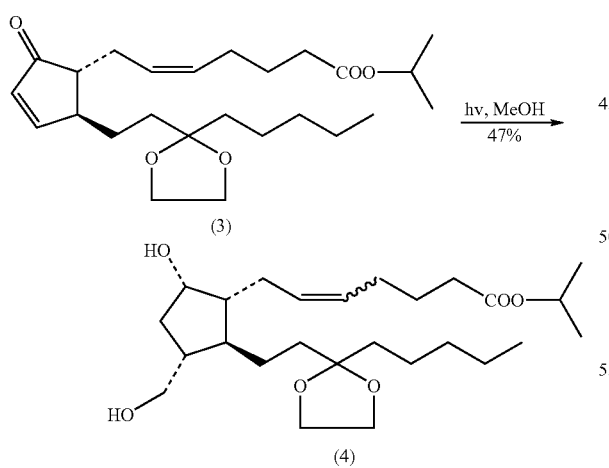

Isopropyl (Z)-7-[(1R,2S)-2-(3,3-ethylenedioxydecyl)-5-oxo-cyclopent-3-enyl]hept-5-enoate (3) (0.81 g) and benzophenone were dissolved in methanol. Under argon atmosphere, the solution was irradiated with 300-W high-pressure mercury lamp for 4 hours and 40 minutes. After evaporation of the solvent, the crude product was chromatographed on silica gel (n-hexane/ethyl acetate=3/2) to give isopropyl-7-[(1R,2S,3R)-2-(3,3-ethylenedioxydecyl)-3-hydroxymethyl-5-oxocyclopentyl]hept-5-enoate (4). Yield 0.41 g, 47%.

4. Preparation of Isopropyl-7-[1R,2S,3R)-2-(3,3-ethylenedioxydecyl)-5-oxo-3-(p-toluenesulfoxymethyl)cyclopentyl]hept-5-enoate (5)

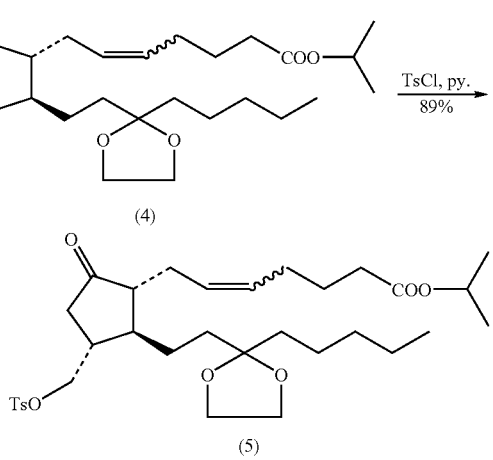

Isopropyl-(1R,2S,3R)-2-(3,3-ethylenedioxydecyl)-3-hydroxymethyl-5-oxocyclopentyl]hept-5-enoate (4) (0.21 g) and pyridine (0.07 g) were dissolved in dichloromethane. To this solution, tosyl chloride (0.17 g) was added at 0° C., and the mixture was stirred for 72 hours. After the usual work-up, the crude product was chromatographed on silica gel to give isopropyl 7-(1R,2S,3R)-2-(3,3-ethylenedioxydecyl)-5-oxo-3-(p-toluenesulfoxy)methylcyclopentyl]hept-5-enoate (5). Yield 0.25 g, 89%.

5. Preparation of Isopropyl-7-[(1R,2R,3R)-2-(3,3-ethylenedioxydecyl)-3-iodemethyl-5-oxocyclopentyl]hept-5-enoate (6)

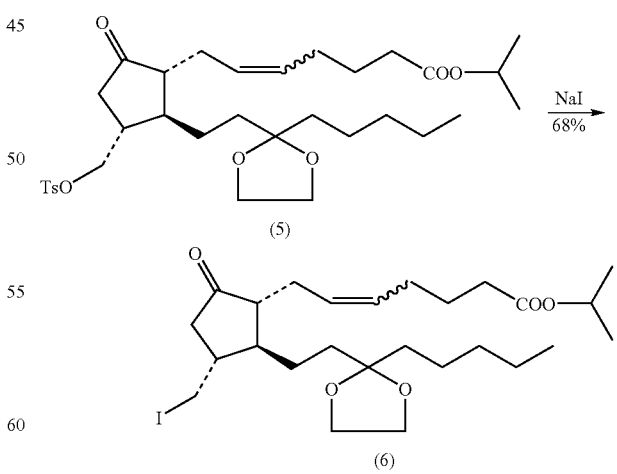

Isopropyl 7-(1R,2S,3R)-2-(3,3-ethylenedioxydecyl)-5-oxo-3-(p-toluenesulfoxy)methylcyclopentyl]hept-5-enoate (5) (0.25 g) was dissolved in acetone, and sodium iodide (0.12 g) was added. The mixture was refluxed for 3 hours. Sodium iodide (0.097 g) was added to the mixture, and the mixture was refluxed for additional 80 minutes. After the usual work-up, the crude product was chromatographed on silica gel (n-hexane/ethyl acetate=5/1) to give isopropyl 7-(1R,2R,3R)-2-(3,3-ethylenedioxydecyl)-3-iodemethyl-5-oxocyclopentyl]hept-5-enoate (6). Yield 0.16 g, 68%.

6. Preparation of Isopropyl 7-(1R,2R,3R)-3-iodemethyl-5-oxo-2-(3-oxodecyl)cyclopentyl]hept-5-enoate (7)

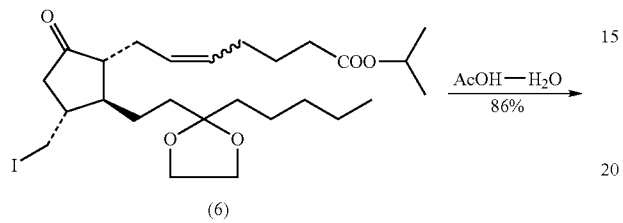

Isopropyl 7-(1R,2R,3R)-2-(3,3-ethylenedioxydecyl)-3-iodemethyl-5-oxocyclopentyl]hept-5-enoate (6) (0.16 g) was dissolved in a mixed solvent of acetic acid/water/tetrahydrofuran (3/1/1). The mixture was stirred for 20 hours at room temperature and for 2.5 hours at 50° C. After evaporation of the solvent, the obtained residue was chromatographed on silica gel (n-hexane/ethyl acetate=1/1) to give isopropyl 7-(1R,2R,3R)-3-iodemethyl-5-oxo-2-(3-oxodecyl)cyclopentyl]hept-5-enoate (7). Yield. 0.13 g; 86%.

7. Preparation of Isopropyl 7-(1S,3S,6S,7R)-3-heptyl-3-hydroxy-bicyclo[4.3.0]nonane-8-one-7-yl]hept-5-enoate (8a) and Isopropyl 7-(1S,3R, 6S, 7R)-3-heptyl-3-hydroxy-bicyclo[4.3.0]nonane-8-one-7-yl]hept-5-enoate (8b)

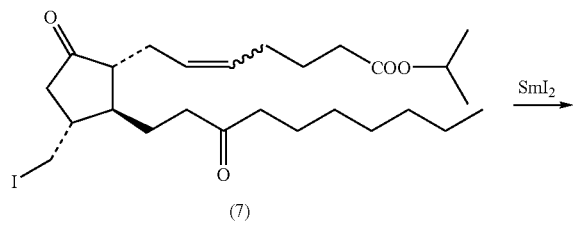

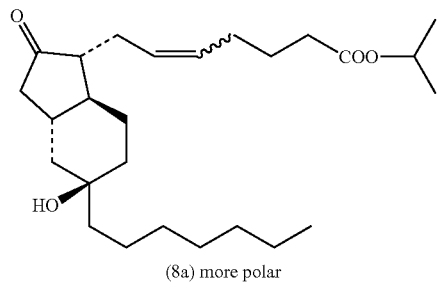

(8a) more polar

+

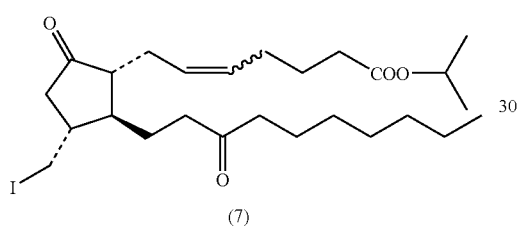

(8b) less polar

Isopropyl 7-(1R,2R,3R)-3-iodemethyl-2-(3-oxodecyl)-5-oxocyclopentyl]hept-5-enoate (7) (0.0574 g) and zirconocene dichloride were dissolved in tetrahydrofuran. The mixture was sonicated under argon stream to purge the air out from the mixture. To the mixture samarium iodide in tetrahydrofuran (0.1 M, 2.1 mL) was added dropwise. The mixture was stirred for 30 minutes at room temperature, and then hydrochloric acid (0.1 M, 1 mL) was added. After the usual work-up, the crude product was chromatographed on silica gel (n-hexane/ethyl acetate=5/1). Two bicyclic products, more polar (8a) and its epimer, less polar (8b) and starting material (7) were obtained as follows:

Isopropyl 7-(1S,3S,6S,7R)-3-heptyl-3-hydroxy-bicyclo[4.3.0]nonane-8-one-7-yl]hept-5-enoate (8a) and Isopropyl 7-(1S,3R,6S,7R)-3-heptyl-3-hydroxy-bicyclo[4.3.0]nonane-8-one-7-yl]hept-5-enoate (8b): Yield 8(a) 5.1 mg, Yield 8(b) 7.2 mg, Recovery of starting material (7) 26.7 mg.

A theoretical synthesis for a compound represented by Formula (I) where Z is a sulfur atom and $W_1$ is an —OH group is set forth below:

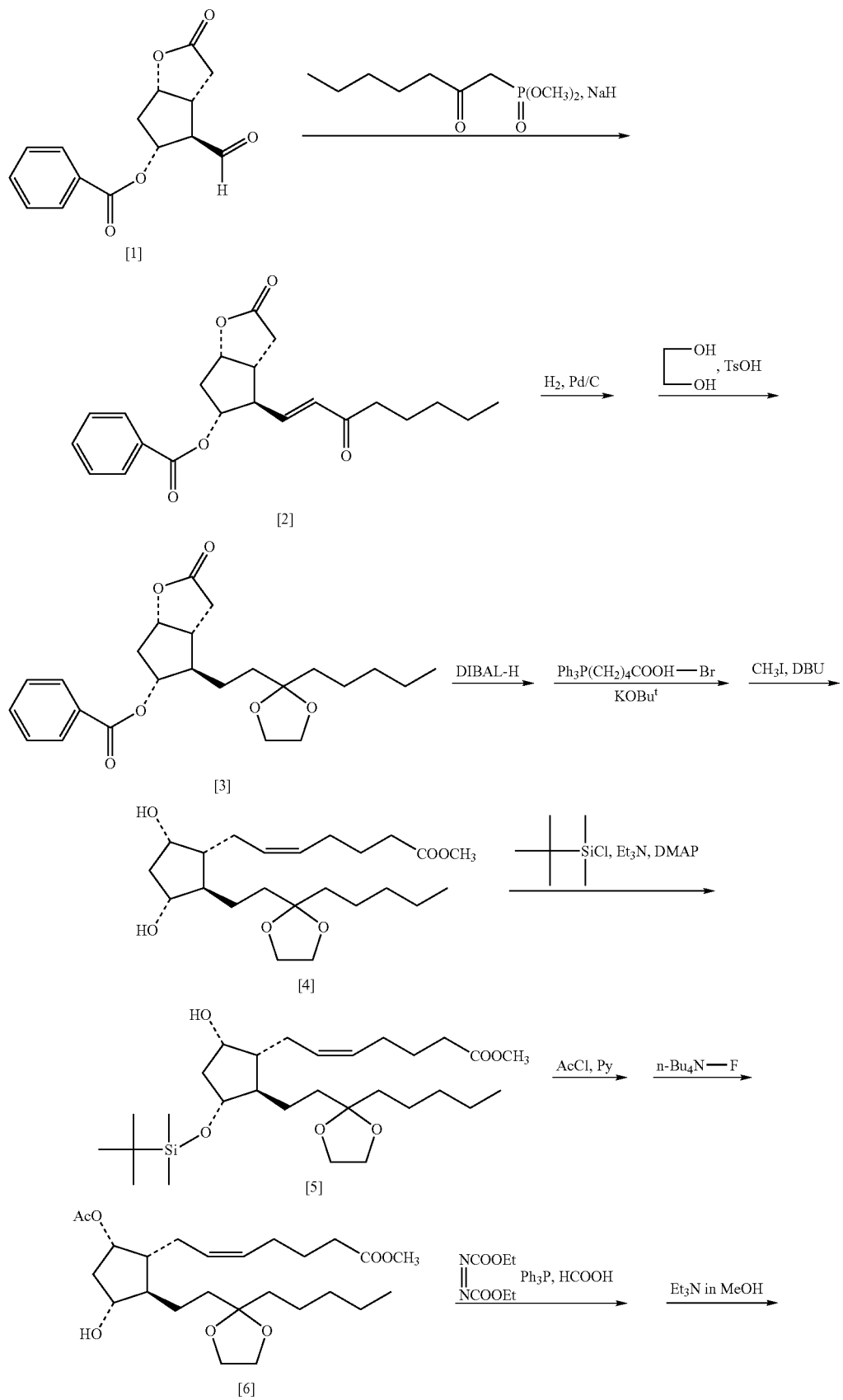

-continued
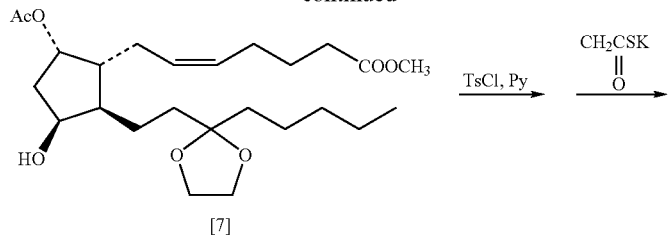
[7]
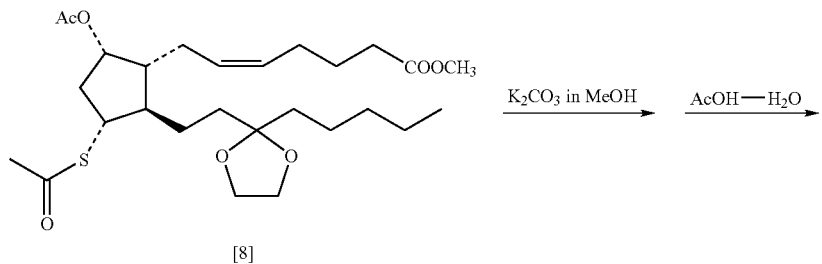
[8]
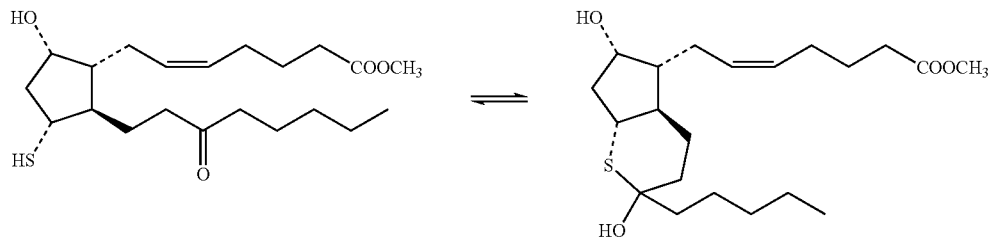
[9] 11-Thia-PGF
| n-Bu$_4$N—F: | tetrabutylammonium fluoride |
| DBU: | 1,8-diazabicyclo[5.4.0]undec-7-ene |
| DIBAL-H: | diisobutylaluminum hydride |
| DMAP: | 4-dimethylaminopyridine |
| NaBH$_4$: | sodium borohydride |
A theoretical synthesis for a compound represented by Formula (I) where Z is a sulfur atom and $W_1$ is a keto is set forth below:
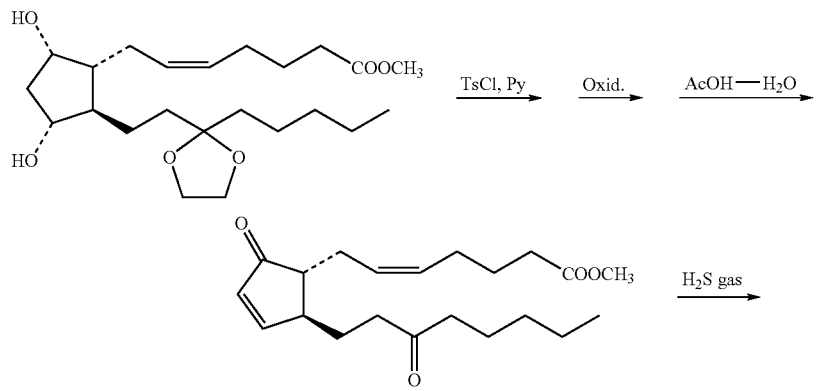

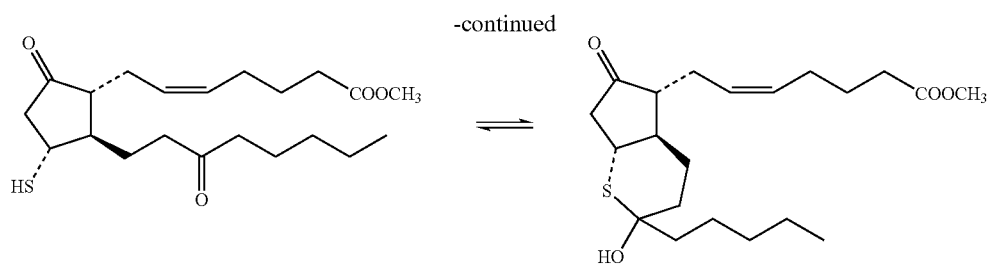
A theoretical synthesis for a compound represented by Formula (I) where Z is a sulfur atom, $W_1$ is a keto and $X_1$ and $X_2$ are fluorine atoms is set forth below:
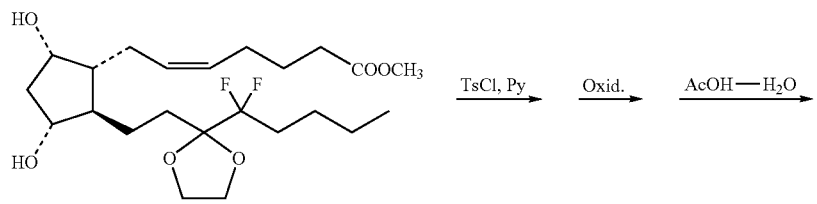
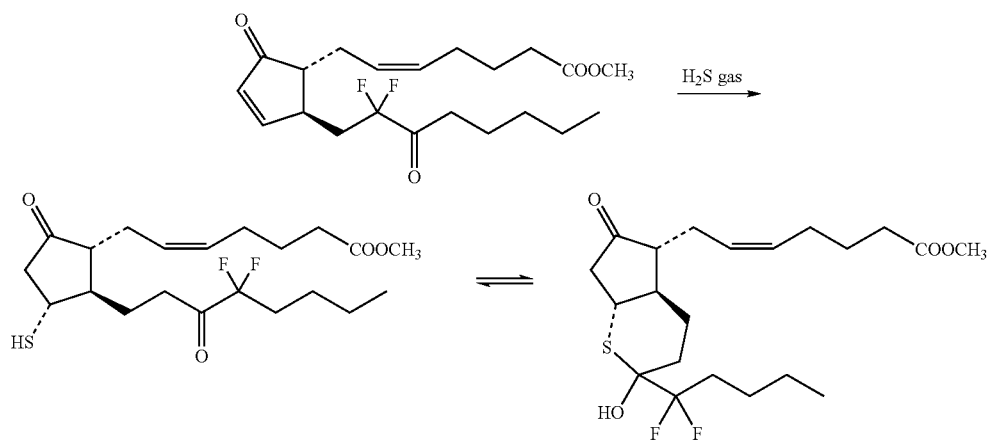
A theoretical synthesis for a compound represented by Formula (I) where Z is a nitrogen atom is set forth below:
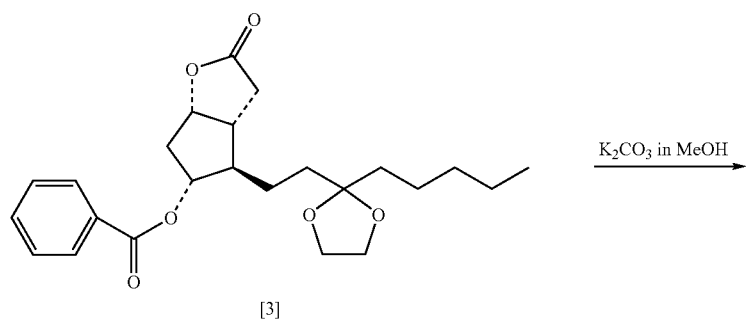
[3]

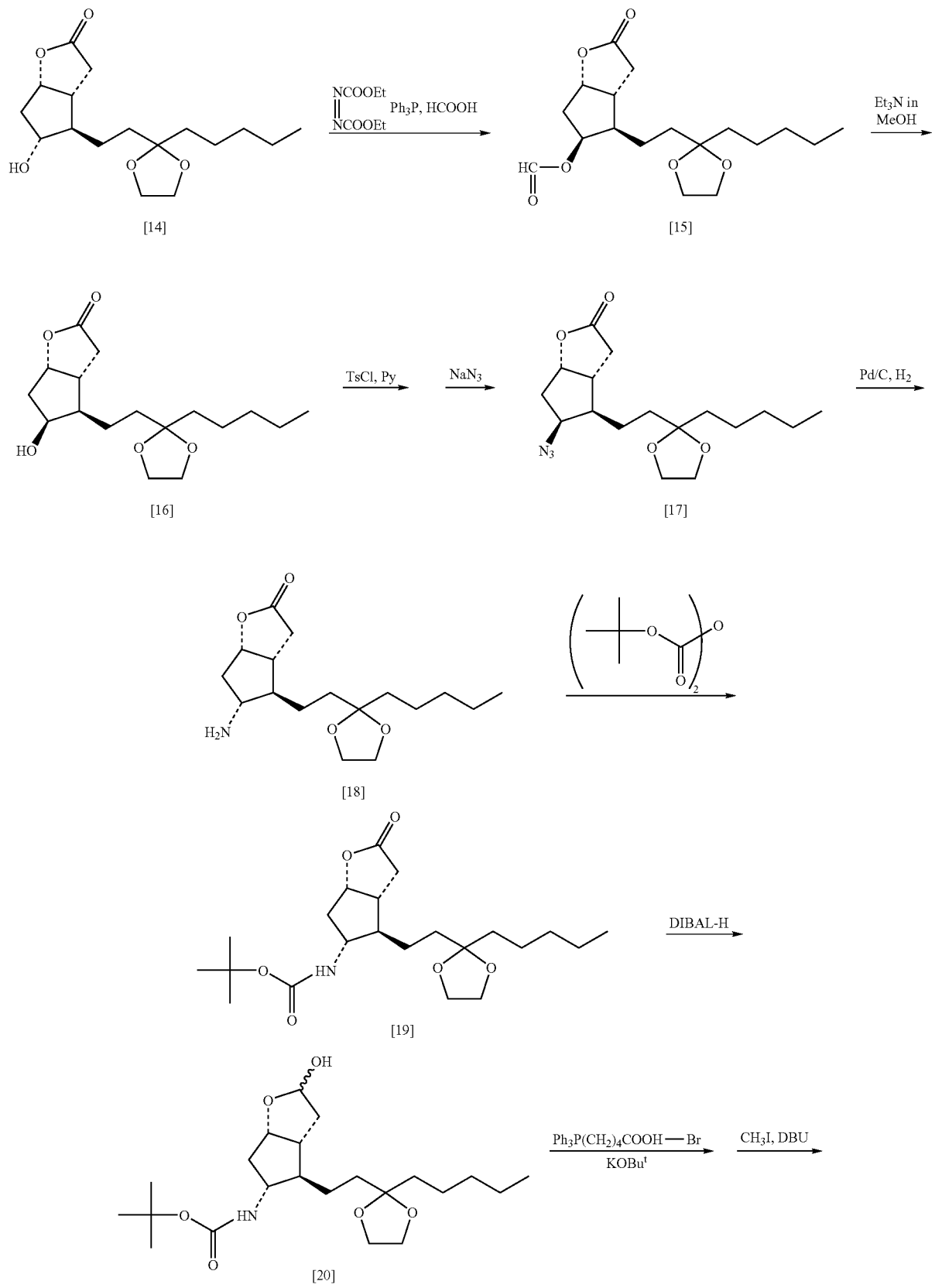

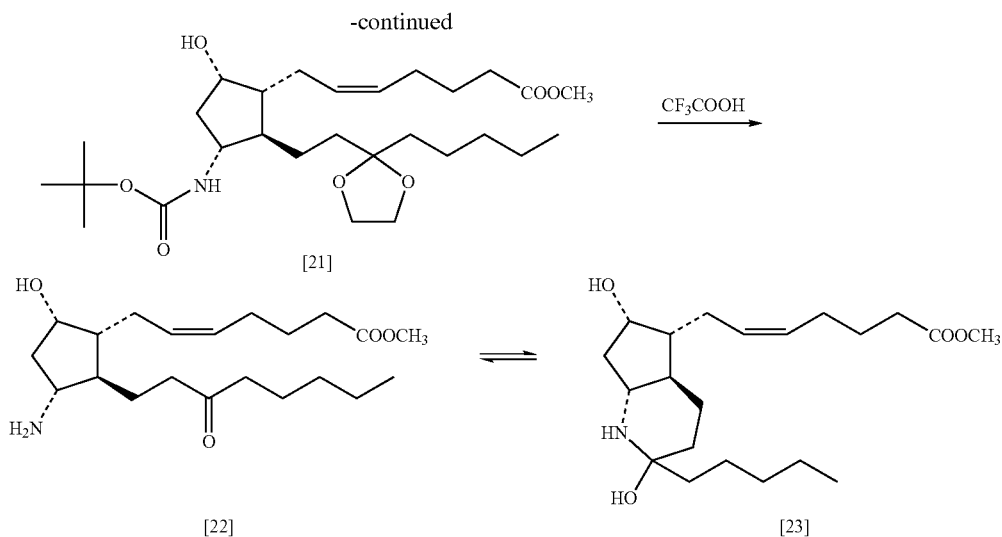
Another theoretical synthesis of a compound represented by Formula (I) where Z is a nitrogen atom is set forth below:
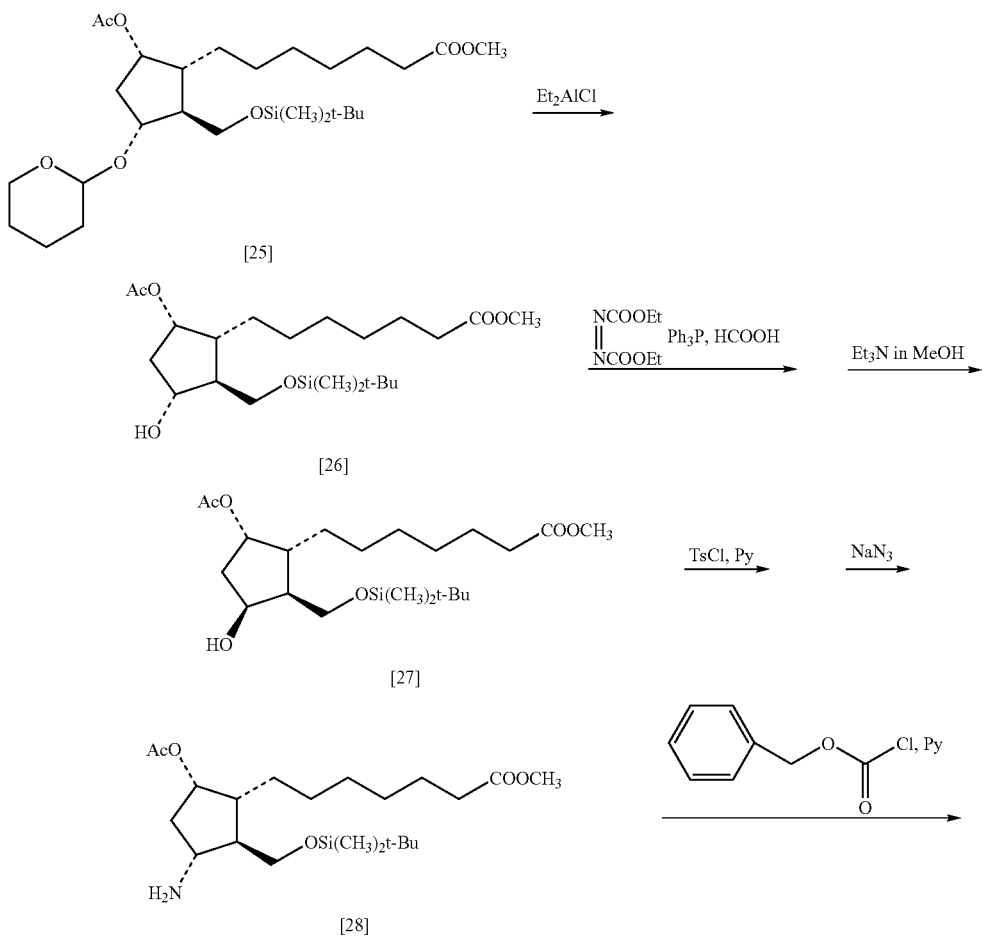

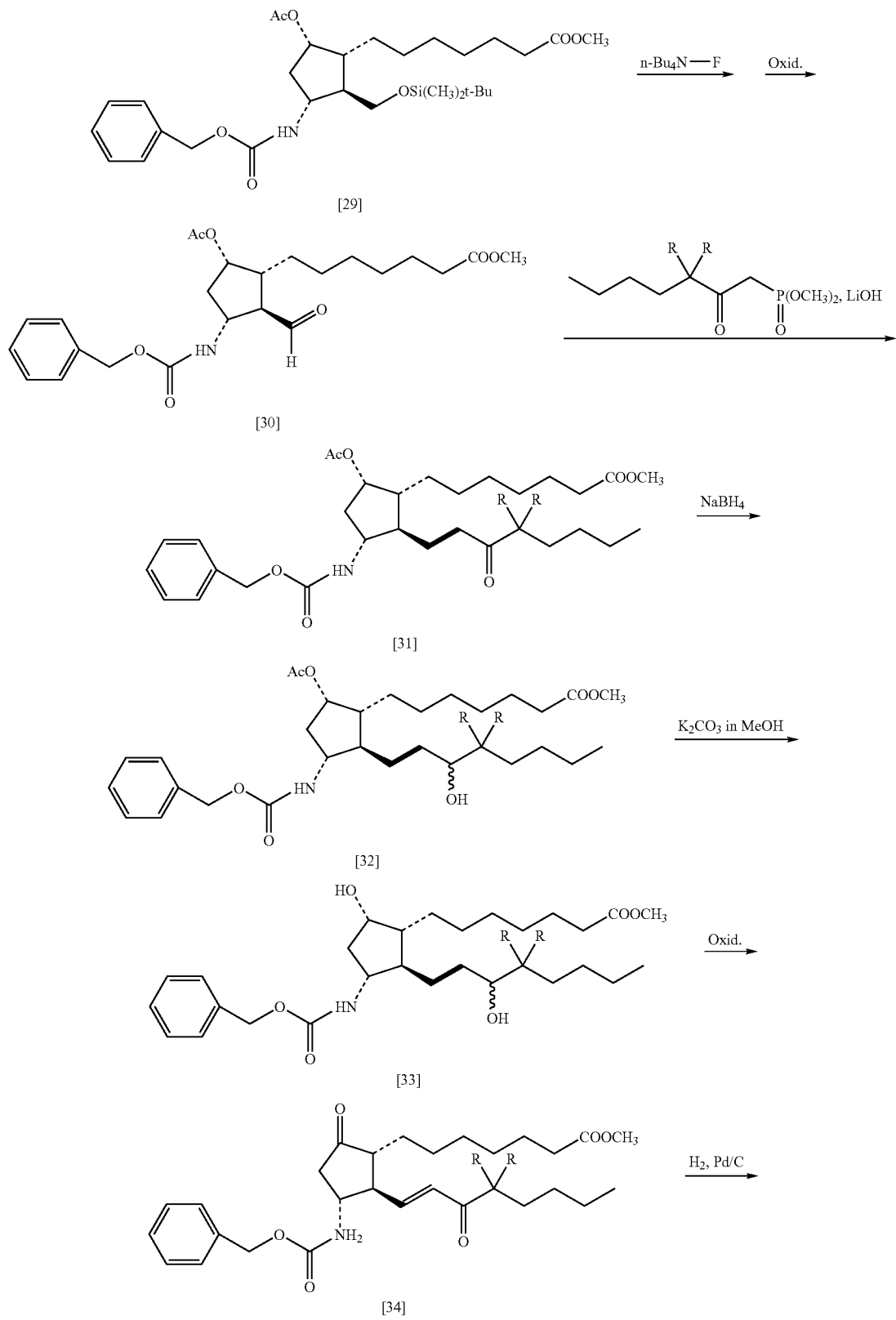

-continued

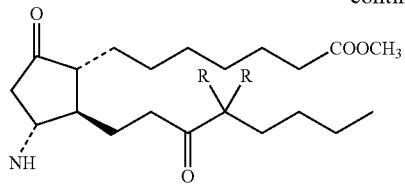

[35]

R—H or F

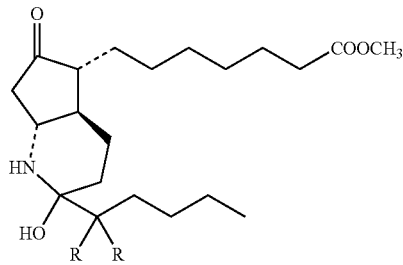

[36]

The preparations in the present invention are not construed to be limited to them, and suitable means for protection, oxidation, reduction and the like may be employed.

The composition of the present invention comprises the above described bi-cyclic compound and a glyceride. Examples of the glyceride used in the present invention include a glyceride of a saturated or unsaturated fatty acid which may have a branched chain. Preferred fatty acid is a medium chain or higher chain fatty acid having at least C6, preferably C6-24 carbon atoms, for example caproic acid (C6), caprylic acid (C8), capric acid (C10), lauric acid (C12) and myristic acid (C14), palmitic acid (C16), palmitoleic acid (C16), stearic acid (C18), oleic acid (C18), linoleic acid (C18), linolenic acid (C18), ricinolic acid (C18) and arachic acid (C20).

In addition, 2 or more glycerides may be used as a mixture.

Examples of the mixture of glycerides are mixture of caprylic acid triglyceride and capric acid triglyceride, vegetable oils such as castor oil, corn oil, olive oil, sesame oil, rape oil, salad oil, cottonseed oil, camellia oil, peanut oil, palm oil, sunflower oil.

The composition of the present invention may be generally prepared by dissolving or admixing the above-disclosed bi-cyclic compound in the glyceride. When it is difficult to dissolve the bi-cyclic compound directly in the glyceride, each of them may be dissolved in a solvent in which both of them are soluble respectively, and then the solutions may be combined. In this embodiment, the solvent may be removed under vacuum.

According to the present invention, the amount of the glyceride relative to that of the bi-cyclic compound is not limited in so far as the object of the invention, that is, stabilization of the bi-cyclic compound is attained. Generally, 1-5,000,000 parts by weight, preferably, 5-1,000,000 parts by weight, and more preferably, 10-500,000 parts by weight of the glyceride may be employed per one part by weight of the bi-cyclic compound.

The composition of the present invention may comprise the other oil solvent. Examples of the other oil solvents may include mineral oils such as liquid paraffin and light liquid paraffin, tocopherol, and the like.

The ratio of the glycerides to the other oil solvent is not limited. The glycerides may present in an amount that improve at least the stability of the bi-cyclic composition of the present invention. The ratio of the glycerides in total oil solvent is at least 1 v/v %, preferably not more than 5 v/v %.

In a preferred embodiment, the composition of the present invention is substantially free of water. The term "substantially free of water" means that the composition does not contain water that is intentionally added. It is understood that many materials contain water that is taken up from the atmosphere or is present as a coordination complex in its normal state. Water taken up by hygroscopic materials or present as a hydrate is permissibly present in the compositions of this embodiment. According to the embodiment, any water that is present in the composition should not be present in amounts such that the water will have a deleterious effect to the composition of the present invention.

The composition of the present invention may further contain physiologically acceptable additives which do not provide adverse effect to the stability of the compound of the formula (I). The additives which may be employed in the present invention include, but not limited to, excipients, diluents, fillers, solvents, lubricants, adjuvants, binders, disintegrants, coatings, capuslating agents, ointment bases, suppository base, aerozoles, emulsifiers, dispersing agents, suspensions, viscosity increasing agents, isotonic agents, buffers, analgesic agents, preservatives, anti-oxidants, corrigents, flavors, colorants, and functional agents such as cyclodextrin, biologically degradable polymers. The details of the additives may be selected from those described in any of general textbooks in the pharmaceutical field. Further, the composition of the present invention may further contain another pharmaceutically active ingredient.

The composition of the present invention may be formulated by a conventional manner. They may be in the form suitable for oral administration, suppository, injection, or topical administration such as eye drops or ointments. Especially, compositions suitable for oral administration such as capsulated compositions and compositions suitable for topical administration such as eye drops are preferable.

The present invention will be explained in more detail by means of the following examples, which are illustrated by way of example only and never intended to limit the scope of the present invention.

EXAMPLE 1

The above-described compounds 1 and 2 were dissolved in the medium chain fatty acid triglyceride (MCT)[3)] at the amount shown in the table 1 below respectively. Each of the solutions was placed in a container made of hard glass and stored at 40° C. The time-course of the content of the compound 1 and 2 in the solutions were determined by HPLC method. The medium chain fatty acid triglyceride used herein was a mixture of caprylic acid triglyceride and capric acid triglyceride (85:15). At the same time, each of the compounds 1 and 2 was placed solely (without being dissolved in the solvent) in the container as above and stored at 40° C. to provide control study.

(1) Under the Absence of the Solvent, the Content of the Compound was Determined as follows (HPLC Method)

The stored compounds 1 and 2, and standard compounds 1 and 2 were weighed precisely around 0.025 g each, and exactly 5 ml aliquots of an internal standard solution were added to the respective weighed compounds. Then the test and standard preparations were obtained by adding acetonitrile (liquid chromatograph grade) to give the precise total amount of 10 ml each. Each 10 µl of the test and standard preparations was loaded on liquid chromatograph and determined the content of the compound by internal standard method with one point calibration curve.

$$\text{content (\%)} = \frac{Q_T}{Q_S} \times W_s \times \frac{100}{W_T}$$

$W_S$: The amount of the compound in the standard preparation (mg)
$W_T$: The amount of the compound 1 or 2 in the test preparation
$Q_S$: Peak area ratio of the compound in the standard preparation to the internal standard.
$Q_T$: Peak area ratio of the compound in the test preparation to the internal standard.

Measurement Conditions
Detector: Ultraviolet absorption spectrophotometer (wavelength: 294 nm)
Column: A stainless tube having about 5 mm of internal diameter and about 25 cm of length, packed with 5 µm octadecylsilyl silica gel for liquid chromatograph
Column temperature: Stable at around 35° C.
Mobile phase: Mixed solution of acetonitrile (liquid chromatograph grade)/aqueous sodium acetate (0.01 mol/l)/ glacial acetic acid (800:200:1)

(2) Under the Presence of the Solvent, the Content of the Compound was Determined as follows (HPLC Method)

Based on the value expressed in the table 1, an amount of the solution corresponding to 36 µg of the compound 1 or 2 was weighted precisely. Precisely 1.0 ml of an internal standard solution was added, and then ethyl acetate (liquid chromatograph grade) was added to give the total amount of 10 ml each. Each 0.1 ml of the solution was vacuum concentrated to dryness to give the test preparation.

Each 18 mg of the respective standard compounds was weighted precisely and admixed with ethyl acetate (liquid chromatograph grade) to give the total amount of exactly 50 ml each. One (1.0) ml of the solution and 10.0, ml of the internal standard solution were measured precisely and admixed with ethyl acetate (liquid chromatograph grade) to give the total amount of 100 ml each. Each 0.1 ml of the solution was vacuum concentrated to dryness to give the standard preparation.

To the test and standard preparations, 0.1 ml of fluorescent labeling reagent and 0.85 ml of fluorescent labeling catalyst were added respectively, and the mixture was stirred and reacted at room temperature more than 30 minutes. 0.05 ml aliquots of acetonitrile (liquid chromatograph grade) containing 2% acetic acid were added to the reaction mixtures respectively, stirred and then stand for more than 30 minutes to provide test and standard solutions.

Each 10 µl of the test and standard solutions was loaded on liquid chromatograph and determined the content of the respective compounds by internal standard method with one point calibration curve.

$$\text{content (\%)} = \frac{Q_T}{Q_S} \times W_s \times \frac{100}{18}$$

$W_S$: The amount of the compound in the standard preparation (mg)
$Q_S$: Peak area ratio of the compound in the standard preparation to the internal standard
$Q_T$: Peak area ratio of the compound in the test preparation to the internal standard.

Measurement Condition
Detector: fluorescent spectrometer (excitation wavelength 259 nm, fluorescent wavelength 394 nm)
Column: A stainless tube having about 5 mm of internal diameter and about 25 cm of length, packed with 5 µm octadecylsilyl silica gel for liquid chromatograph
Column temperature: Stable at around 35° C.
Mobile phase: Mixed solution of acetonitrile (liquid chromatograph grade)/methanol (liquid chromatograph grade)/ aqueous ammonium acetate (0.05 mol/l) (4:11:5)

The results are shown in Table 1 below.

TABLE 1

| | | Time course of the contents of the compounds 1 and 2 stored at 40° C. (%) | | | | | | | |
|---|---|---|---|---|---|---|---|---|---|
| compound | solvent | initial | 6 days | 7 days | 14 days | 28 days | 38 days | 90 days | 191 days |
| compound 1 | crystal | 100 | — | 97.2 | 94.1 | 87.4 | — | — | — |
| | MCT[1] | 100 | — | — | 101.4 | — | 102.1 | 100.9 | — |
| compound 2 | crystal | 100 | 84.5 | — | 75.0 | 53.4 | — | — | — |
| | MCT[2] | 100 | — | — | 99.6 | 98.9 | — | — | 99.6 |

[1] compound 1/solvent: 0.36 mg/g
[2] compound 2/solvent: 0.12 mg/g
[3] mixture of caprylic acid triglyceride and capric acid triglyceride (85:15)

From the results shown in Table 1, it was proved that the stability of the compounds 1 and 2 were significantly improved by admixing the same with the glyceride according to the present invention.

EXAMPLE 2

The above-described compound 1 was dissolved in various solvents at the amount shown in the table 2 below respectively. Each of the solutions was placed in a container made of low-density polyethylene (LDPE), hard glass or stainless steel and stored at 40° C. The content of the compound 1 in the solutions after four weeks were determined by HPLC method according to the above described (2) of Example 1 except for using composition shown in table 2 below.

The results are shown in Table 2 below.

TABLE 2

Stability of the compound 1 stored at 40° C. for 4 weeks in various solvent

| conc. of compound 1 | solvent | container | % to the initial 4 weeks after |
|---|---|---|---|
| 10 µg/mL | MCT[1] | LDPE[2] | 100.8 |
| 20 µg/mL | MCT | Hard glass | 99.5 |
| 20 µg/mL | MCT | Stainless steel | 99.5 |
| 20 µg/mL | Caster oil | LDPE | 102.9 |
| 20 µg/mL | Corn oil | LDPE | 99.6 |
| 20 µg/mL | Olive oil | LDPE | 99.0 |
| 20 µg/mL | Sesame oil | LDPE | 100.1 |
| 20 µg/mL | Diluted water | Hard glass | 39.6 |
| 10 µg/mL | Saline | Hard glass | 18.0 |

[1]MCT: mixture of caprylic acid triglyceride and capric acid triglyceride (85:15)
[2]LDPE: low-density polyethylene From the results shown in Table 2, it was proved that the stability of the compound 1 were significantly improved by admixing the same with the glyceride according to the present invention.

EXAMPLE 3

The above-described compound 1 was dissolved in various ratio of MCT to Mineral oil at the amount shown in the table 3 below respectively. Each of the solutions was placed in a container made of LDPE and stored at 40° C. The content of the compound in the solutions after four weeks were determined by HPLC method according to the above described (2) of Example 1 except for using composition shown in table 3 below.

TABLE 3

Stability of the compound 1 stored at 40° C. for 4 weeks in various ratio of MCT to Mineral oil

| conc. of compound 1 | MCT/MO[1] (V/V) | % to the initial 4 weeks after |
|---|---|---|
| 0.7 µg/mL | 0/100 | 88.3 |
| 0.5 µg/mL | 1/99 | 91.0 |
| 0.5 µg/mL | 2/98 | 96.6 |
| 0.5 µg/mL | 5/95 | 98.1 |
| 0.5 µg/mL | 10/90 | 99.0 |
| 10 µg/mL | 50/50 | 101.9 |

[1]MO: mineral oil

From the results shown in Table 3, it was proved that the stability of the compound 1 were significantly improved by admixing the same with the mixture of glyceride and other oil solvent according to the present invention.

FORMULATION EXAMPLE 1

Capsule

Fifty (50) micrograms of compound 1 was dissolved in MCT to give total amount of 100 mg, and filled in a capsule in the conventional way to give a capsule form.

FORMULATION EXAMPLE 2

Eye drops

Two point five (2.5) micrograms of compound 1 was dissolved in MCT/Mineral oil (20:80) to give total volume of 5 ml. The solution was filled in an eye-drop container to give an eye drop composition.

What is claimed is:
1. A composition comprising:
   i: the following bi-cyclic compound

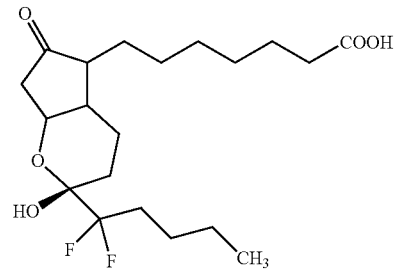

7-[(1R,3R,6R,7R)-3-(1,1-difluoropentyl)-3-hydroxy-2-oxabicyclo[4.3.0]nonane-8-one-7-yl]heptanoic acid,
   ii. the mono-cyclic tautomer of said compound; and
   iii. at least one glyceride,
   wherein the ratio of the bi-cyclic compound to mono-cyclic tautomer is at least 90:10.
2. The composition according to claim 1, wherein the ratio of bi-cyclic compound to mono-cyclic tautomer is substantially 100:0.
3. The composition according to claim 1, wherein said glyceride has between 6 and 24 carbon atoms.
4. The composition according to claim 1, wherein said glyceride has between 6 and 20 carbon atoms.
5. The composition according to claim 1, in which the glyceride is a mixture of 2 or more glycerides.
6. The composition according to claim 1, wherein at least one glyceride is a triglyceride.
7. The composition according to claim 2, wherein at least one glyceride is a triglyceride.
8. The composition according to claim 6, wherein said triglyceride is caprylic acid triglyceride and/or capric acid triglyceride.
9. The composition according to claim 6, wherein the triglyceride is present in an amount of 1-5,000,000 parts by weight based on one part by weight of the bi-cyclic structure.
10. The composition according to claim 6, wherein the triglyceride is present in an amount of 5-1,000,000 parts by weight based on one part by weight of the bi-cyclic structure.
11. The composition according to claim 6, wherein the triglyceride is present in an amount of 10-500,000 parts by weight based on one part by weight of the bi-cyclic structure.
12. The composition according to claim 1, wherein said glyceride is admixed with other oil solvent.
13. The composition according to claim 12, wherein said other oil solvent is mineral oil.
14. The composition according to claim 1, which is in a dosage form suitable for oral administration.
15. The composition according to claim 14, which is formulated as a capsule.
16. The composition according to claim 1, which is in a dosage form suitable for topical administration.

17. The composition according to claim 16, which is formulated as an eye drop.

18. A composition comprising:
i. the following bi-cyclic compound

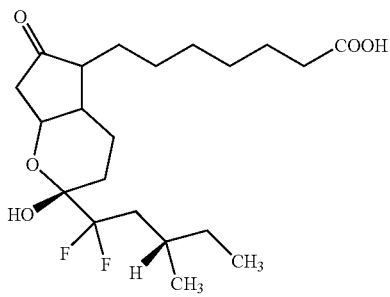

7-[(1R,6R,7R)-3-[(3S)-1,1-difluoro-3-methylpentyl]-3-hydroxy-2-oxabicyclo[4.3.0]nonane-8-one-7-yl]heptanoic acid,
ii. the mono-cyclic tautomer of said compound; and
iii. at least one glyceride,
wherein the ratio of the bi-cyclic compound to mono-cyclic tautomer is at least 1:1.

19. The composition according to claim 18, wherein the ratio of bi-cyclic compound to mono-cyclic tautomer is at least 90:10.

20. The composition according to claim 18, wherein the ratio of bi-cyclic compound to mono-cyclic tautomer is substantially 100:0.

21. The composition according to claim 18, wherein said glyceride has between 6 and 24 carbon atoms.

22. The composition according to claim 18, wherein said glyceride has between 6 and 20 carbon atoms.

23. The composition according to claim 18, in which the glyceride is a mixture of 2 or more glycerides.

24. The composition according to claim 18, wherein at least one glyceride is a triglyceride.

25. The composition according to claim 24, wherein said triglyceride is caprylic acid triglyceride and/or capric acid triglyceride.

26. The composition according to claim 24, wherein the triglyceride is present in an amount of 1-5,000,000 parts by weight based on one part by weight of the bi-cyclic structure.

27. The composition according to claim 24, wherein the triglyceride is present in an amount of 5-1,000,000 parts by weight based on one part by weight of the bi-cyclic structure.

28. The composition according to claim 24, wherein the triglyceride is present in an amount of 10-500,000 parts by weight based on one part by weight of the bi-cyclic structure.

29. The composition according to claim 24, wherein said glyceride is admixed with other oil solvent.

30. The composition according to claim 29, wherein said other oil solvent is mineral oil.

31. The composition according to claim 18, which is in a dosage form suitable for oral administration.

32. The composition according to claim 31, which is formulated as a capsule.

33. The composition according to claim 18, which in a dosage form suitable for topical administration.

34. The composition according to claim 33, which is formulated as an eye drop.

* * * * *